United States Patent [19]

Adams

[11] 4,036,230
[45] July 19, 1977

[54] MEDICINAL INSERT INSTRUMENT

[76] Inventor: Kenneth Waldock Adams, 414 Pocatello Road, Middletown, N.Y. 10940

[21] Appl. No.: 715,319

[22] Filed: Aug. 18, 1976

[51] Int. Cl.² .............................................. A61N 7/00
[52] U.S. Cl. .................................. 128/269; 128/2 W; 128/260; 128/20
[58] Field of Search ................ 128/2 W, 260, 269, 20, 128/249, 233; 356/88.7, 244

[56] References Cited

U.S. PATENT DOCUMENTS

| | | | |
|---|---|---|---|
| 2,969,057 | 1/1961 | Simmons | 128/2 W |
| 3,054,398 | 9/1962 | Kobler | 128/20 |
| 3,439,674 | 4/1969 | Lelicoff | 128/249 |
| 3,884,232 | 5/1975 | Braun | 128/260 |
| 3,965,888 | 6/1976 | Bender | 128/2 W |

Primary Examiner—Aldrich F. Medbery

[57] ABSTRACT

A medicinal, substantially elliptically shaped insert is easily placed into, or removed from, the eye by a wand-like instrument. The instrument has an elongated stem which is held in the hand, generally between the thumb and index finger. One end of the stem supports an applicator portion. The applicator portion carries the insert by wet adhesion and generally conforms to, and is aligned with, the substantially elliptical shape of the insert. This configuration allows for the ease of placement of the insert transversely across the eyelid or sclerotic portion of the eye. On an opposite, or distal end of the stem, is a swab-like section for the removal of the insert from the eye. The swab-like section contains, or is coated with, an adhesive material, which when placed in contact with the insert, will easily lift the insert from the eye.

15 Claims, 16 Drawing Figures

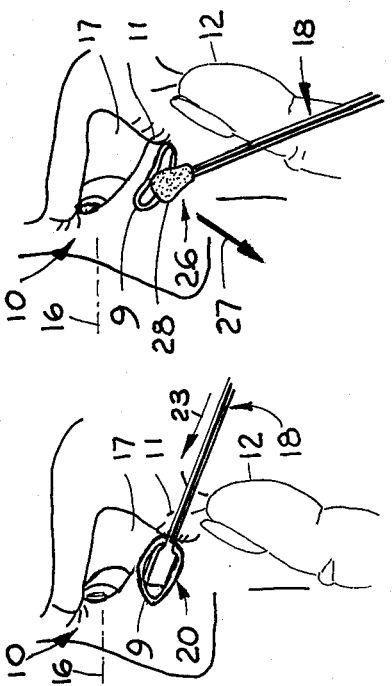
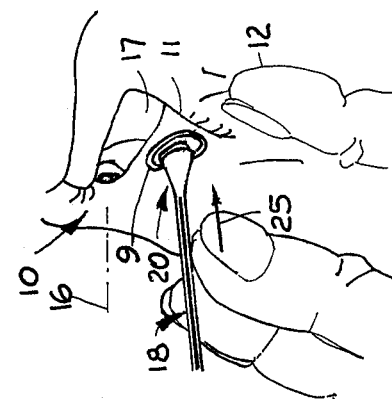
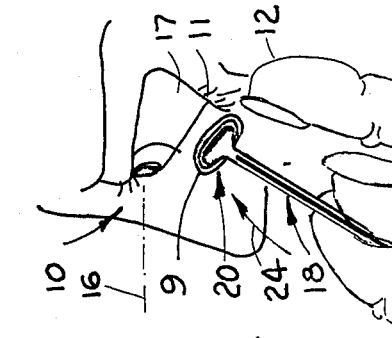
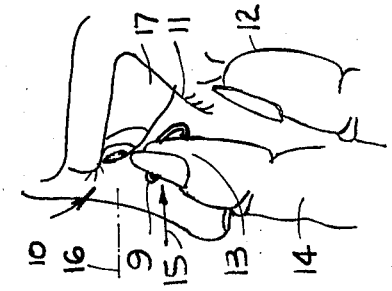
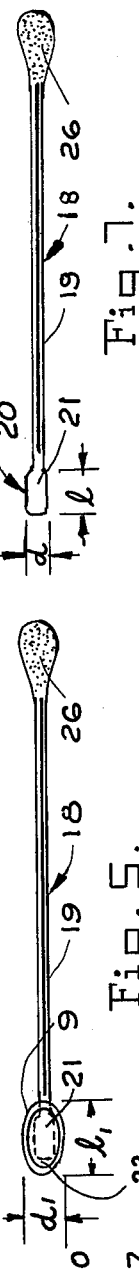
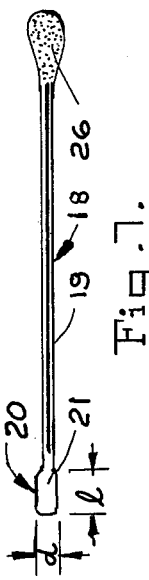
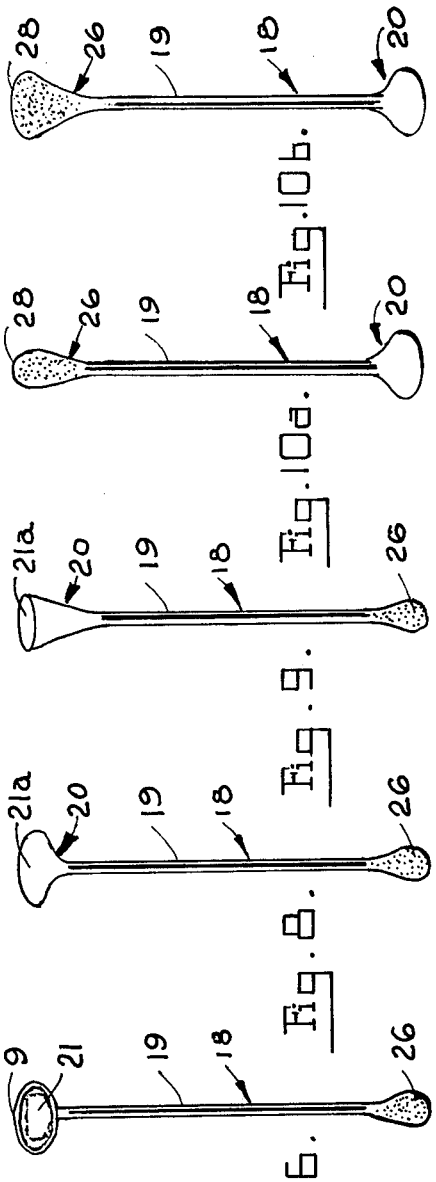

MEDICINAL INSERT INSTRUMENT

The invention pertains to an instrument for facilitating the use of a medicinal insert in the eye, and more particularly for an applicator-type instrument for placing into, and/or removing a medicinal, substantially elliptical insert from the eye.

BACKGROUND OF THE INVENTION

In recent times, an insert has been invented that dispenses medicine into the eye at a controlled rate. Such timed-release, medicinal inserts are placed within the eye, and generally rest under the eyelid. When the medicine in the insert is exhausted, the insert is removed from the eye, and a fresh insert is inserted. One such insert of the aforementioned type is called an Ocusert, manufactured by Alza Pharmaceuticals, Division of Alza Corporation, Palo Alto, Calif.

At present, the recommended way of placing the above insert into the eye is by pulling the lower eyelid down with one hand, while placing the insert into the eye with the finger tip of the other hand. To remove the insert, the recommended procedure suggests pinching the insert between the thumb and forefinger of the hand, and pulling the insert from the eye.

While may users of the insert find the above procedures fairly convenient, many others do not. Because of the natural reflex action of the eye to approaching foreign bodies, the movement of the hand towards the eye in placing or removing the insert is usually accompanied by traumatic twitching. Thus, many people find it difficult to use the insert, and in fact quite a few can never adapt to its use.

The present invention seeks to provide an instrument that will greatly facilitate the placement or removal of the insert, so that practically all potential users can easily adapt to its use. In addition, the inventive instrument will be found to be quite useful by doctors and ophthalmologists when first acquainting their patients to the use of the insert.

SUMMARY OF THE INVENTION the invention relates to an instrument for easily placing into, or removing from, the eye, a medicinal insert having a substantially elliptical shape. The instrument has an elongated stem which is held in the hand, generally between the thumb and index finger. One end of the stem supports an applicator portion. The insert is attached to the applicator end by means of wet adhesion, i.e. the applicator is dipped in water and applied to the insert. The insert will adhere to the applicator surface by capillary attraction.

The applicator with the insert is then placed towards the eye, where the insert attaches to the eyelid or sclerotic portion of the eye by a greater capillary attraction. The eye exerts a greater capillary attraction towards the insert, because the wetted adhesion area between the insert and the eye (eyelid or sclerotic portion) is greater than the wetted adhesion area between the insert and the applicator surface.

The inventive instrument does not produce traumatic effects when placed towards the eye, because of its small profile, and its smaller angle of insertion. In other words, the instrument does not appreciably move into the line of sight of the user.

The applicator portion generally conforms to, and aligns with, the elliptical shape of the insert. This is important in placing the insert transversely across the eye.

On the opposite or distal end of the stem is a swab-like section for the removal of the insert from the eye. The swab-like section contains, or is coated with, an adhesive material. When the adhesive comes in contact with the insert in the eye, the insert will prefer the adhesive swab, and will be easily lifted from the eye.

It is an object of this invention to provide an improved instrument for placing into, and/or removing from, the eye a medicinal insert;

It is another object of the invention to provide an instrument to facilitate the use of an elliptically shaped insert in the eye;

It is a further object of this invention to provide an instrument for use in conjunction with a medicinal insert for the eye, which has a small profile to prevent trauma when moving the instrument towards the eye; and It is but another object of the invention to provide an insert applicator, that conforms to, or otherwise aligns with the insert for the purpose of placing the insert transversely across the eye.

These and other objects of this invention will become more apparent and will be better understood with reference to the following detailed description, taken in conjunction with the accompanying drawings, in which:

FIG. 1 is a side view of a prior art way of inserting a medicinal insert into an eye;

FIG. 1a is a front view of an eye with the medicinal insert in place;

FIG. 2a is a side view of one way to apply a medicinal insert into the eye, using one embodiment of the inventive instrument;

FIG. 2b is a side view of an alternate way to apply the insert using another embodiment of the instrument shown in FIG. 2a;

FIG. 3 is a side view of still another way of applying the insert using yet another embodiment of the inventive instruments shown in FIGS. 2a and 2b;

FIG. 4 is a side view of the inventive instrument depicted in FIG. 3 being used to remove a medicinal insert from the eye;

FIG. 5 is a front view of the embodiment of the instrument shown in FIG. 3 in relation to an insert to be placed in the eye;

FIGS. 5a and 5b show two possible adhesion surface shapes (front view) for the applicator end of the instrument of FIG. 5;

FIG. 6 is a front view of an alternate embodiment of the instrument shown in FIG. 5 in relation to an insert to be placed in the eye;

FIGS. 7, 8, and 9, each are front views of three embodiments of the inventive instrument; and FIGS. 10a and 10b are front views of two embodiments of the swab-like end of the inventive instrument.

DETAILED DESCRIPTION

Now referring to FIG. 1, a prior art method of inserting a medicinal, substantially elliptically shaped insert 9 into an eye 10 is shown. The eyelid 11 is drawn downward by an index finger 12 of one hand, as illustrated. The insert 9 is placed on the finger tip 13 of the index finger 14 of the other hand, and the finger 14 is brought towards the eye (arrow 15). As will be seen, the finger tip 13 has a large profile, and approaches very closely to the line of sight 16 of the eye 10. The object of the prior method is to place the insert 9 transversely across the sclerotic portion 17 or eye 10 as depicted in FIG. 1a. However, because the eye 10 is painfully aware of the approaching presence of the finger tip 13 (FIG. 1), the eye 10 will very often start to twitch by reflex action. As a result, many users of this insert will find it difficult to apply it to the eye. Even more traumatic is the removal of the insert, which requires that the insert 9 be pinched by the thumb and index finger, and then pulled from the eye 10. In such an instance, the eye 10 sees an even larger profile (two fingers) coming towards it. In addition, the insert 9 being moist from being in the eye 10, will be slippery to handle. This will make its removal quite difficult.

Referring to FIGS. 7, 8, 9, respectively, three embodiments of the inventive instrument 18 for placing the insert in the eye are shown. Each instrument 18 has an elongated stem 19. On one end of the stem is an applicator portion, generally illustrated by arrow 20. In FIG. 7, the applicator portion 20 has a rectangular shaped a relatively weak adhesion surface 21 with rounded edges. The lateral dimension $l$ is longer than the longitudinal dimension $d$ of adhesion surface 21. Surface 21 is wetted and then placed on the insert 9 as shown in FIG. 5. The adhesion surface 21 of the applicator portion of the instrument 18 will be placed within the boundaries of an outer surface of the surface of insert 9, and adhere to the insert 9 by capillary attraction. As will be seen, the lateral dimension $l$ will be placed substantially coincident with the lateral dimension $l_1$ of the insert 9. Likewise, the longitudinal dimension $d$ will be placed substantially coincident with the longitudinal dimension $d_1$ of the insert 9. With this alignment, the insert 9 will be easily applied transversely across the eye, as recommended by the manufacture of the insert, and as illustrated in FIG. 1a.

It will be seen, that the surface area of the adhesion surface 21 of the applicator is less than the surface area 22 of the insert 9. Thus, when the insert 9 will be placed in the eye, the capillary attraction of the eye (wetted eye surface) will be greater for the insert surface 22, than the attraction between the insert and adhesion surface 21. Therefore, the insert will be pulled from the applicator portion 20, and seat itself within the eye.

The lateral dimension $l$ of the adhesion surface 21 may be designed to be axially coincident with stem 19 of the instrument 18 as depicted in FIG. 7, or it may be designed to be perpendicular to stem 19, as shown in FIG. 6. The reason for either of the two designs, lies in whether the insert is placed in the eye from the side, as will be hereinafter explained with reference to FIG. 3, or whether it is placed in the eye from below, as will be hereinafter explained with reference to FIG. 2a.

Naturally, the rectangular shape is not the only conforming shape the adhesion surface 21 may have for insert 9. The adhesion surfaces 21a of two other embodiments depicted in FIGS. 8 and 9, are elliptical. The elliptical shape of the adhesion surfaces 21a may actually be preferable to the substantially rectangular shape in conforming to, and aligning with the insert 9. Both surfaces 21a of FIGS. 8 and 9, respectively, also have a smaller surface area than the surface area 22 of insert 9. In this way, they will act in a similar manner when the insert 9 is wetted and placed in the eye.

The difference between surfaces 21 and 21a may be more clearly seen in the front views of these surfaces as offered in FIGS. 5a and 5b.

The embodiment shown in FIG. 9 has the applicator end of instrument 18 in the shape of a golf tee. This instrument will be used in conjunction with the method of placement to be hereinafter explained in FIG. 2b. This method is laterally more straight forward (arrow 23) towards eye 10.

Generally speaking, the inventive instrument 18 makes placement of the insert 9 in eye 10 easier than the prior art for still another reason than: (a) the better approach to the eye; and/or (b) the low profile of the instrument. The instrument 18 makes it easier to place the insert 9 on the lower eyelid 11, as shown in phantom in FIG 1a. This new method of placement is facilitated by use of the instrument 18, and provides an additionally further approach of the insert from the line of sight 16 of the eye 10. This will of course produce less trauma to the eye.

Another incidental advantage of placing the insert 9 on the eyelid 11, is that the user never made direct contact with the eye. This not only reduces trauma, but prevents, or substantially reduces, the risk of injury to the eye.

The placement of insert 9 in the eye 10 by the instruments 18 illustrated in FIGS. 7, 8, and 9, will be explained with reference to FIGS. 3, 2a, and 2b, respectively.

Referring to FIG. 3, a finger 12 is again shown pulling the lower eyelid 11 downwardly. The instrument 18 of FIG. 7 is directed toward the eye 10 from the side (arrow 23). The insert 9 is deposited from the applicator portion 20 onto either the inside of the eyelid 11, or the sclerotic portion 17 of the eye. When the insert 9 is placed from the side as depicted, very little trauma is produced. This is so, because the eye does not see much of the instrument 18, or its approach towards the eye.

Referring to FIGS. 2a, the finger 12 is again lowering the eyelid 11. The instrument 18 of FIG. 8 is directed towards the eye 10 from beneath the eye (arrow 24). As before, the insert 9 is deposited from the applicator portion 20 to the sclerotic portion 17 of the eye, or the inside of the eyelid 11. Again, the eye 10 sees very little of the profile of the instrument, or its approach.

Referring to FIG. 2b, a finger 12 is depressing the lower eyelid 11. The instrument 18 of FIG. 9 is directed towards the eyelid 11 in a forward direction (arrow 25) from below the line of sight 16 of the eye 10. The insert 9 on the applicator portion 20 is deposited on the lower eyelid 11. Once more, the eye 10 sees very little of the instrument profile or its approach towards the eye 10.

In all of the aforementioned methods, very little trauma is produced. The insert 9 is placed transversely across the sclerotic portion 17 of the eye 10 as illustrated in FIG. 1a or transversely across the inside of the lower eyelid 11 as shown in phantom. The conformity and alignment of the applicator portion 20 (either one of the embodiments) with insert 9 helps to properly direct and align the insert 9 across the eye or eyelid.

To remove the insert 9 from the eye 10, reference is made to FIG. 4, and the distal end 26 of instrument 18. Two embodiments are shown for the distal removal section 26 of instrument 18 in FIGS. 10a and 10b, respectively. The inventive removal of the insert 9 from the eye is even easier, and less traumatic than its insertion into the eye. As will be recalled, the prior art method of removal was just the reverse, i.e. the most traumatic of the two procedures (insertion and removal). Thus, the inventive procedure of removing the insert is even more significant than the insertion method.

The removal section 26 has generally a swab-like shape as shown in FIGS. 10a or 10b. The swab contains, or is coated with, an adhesive 28. The swab end 26 of instrument 18 is directed toward the eye containing the insert 9. The eyelid 11 is drawn downwardly by finger 12 to expose the insert 9, which may be resting on either the eyelid 11 or the sclerotic portion 17 of eye 10. The swab 26 is brought in contact with insert 9. The adhesive 28 will cause the insert 9 to stick to the swab 26. The instrument is then pulled (arrow 27) from the eye 10 as illustrated in FIG. 4.

The instruments 18 mentioned in the preceding discussions can be constructed in several ways:

a. The stem 19 can be a rod of metal, wood, plastic, or paper-like material. Portions 20 and 26 may be fastened to the stem 19 as befits the materials being used. The swab end 26 may be made from cotton, while the applicator portion 20 may be made from rubber, plastic, or metal. The adhesive 28 may be similar to that used for surgical adhesive bandages or that used on adhesive tapes. The adhesive 28 should not leave a residue in the eye 10 or be so sticky as to injure the eye if accidently touched to it.

b. The instruments 18 can be made in one integral piece, as when the entire instrument is molded from plastic. Apolypropylene or styrene type plastic may be best for this purpose. The adhesive 28 will be coated on swab end 26.

Having thus described the invention, what is desired to be secured by Letters Patent is presented by the appended claims.

What is claimed is:

1. A hand-held instrument for facilitating the application and/or removal of a medicinal substantially elliptically-shaped insert, to and from an eye, said instrument comprising:
   an elongated wand-like stem to be hand-held for applying said medicinal insert to said eye, said wand-like stem having a first end, and a second end opposite said first end; and
   an applicator section supported upon said first end of said wand-like stem for receiving a medicinal elliptically-shaped insert, and for placing said medicinal insert generally upon a sclerotic or eyelid portion of said eye, said applicator section having a relatively weak adhesion surface area generally less than a surface area of said insert, said applicator section having a shape generally conforming to, and aligning with, said substantially elliptically-shaped insert wherein a lateral dimension of said adhesion surface is greater than a longitudinal dimension thereof and said longitudinal dimension of said adhesion surface of the applicator member being generally coincident with a longitudinal dimension of said insert, and said lateral dimension of said adhesion surface of the applicator being generally coincident with a lateral dimension of said insert, whereby the substantially elliptically shaped insert may be easily directed into, and placed upon, the eye by said applicator section.

2. The hand-held instrument of claim 1, further comprising a removal section supported upon said second end of said wand-like stem, said removal section having an adhesively coated surface for contact with, and adhesion to, said substantially elliptically-shaped insert for the purpose of removing an insert disposed within the eye.

3. The hand-held instrument of claim 1, wherein said applicator section is substantially elliptically-shaped.

4. The hand-held instrument of claim 1, wherein said applicator section is integrally formed with said wand-like stem.

5. The hand-held instrument of claim 1, wherein the longitudinal dimension of the adhesion surface of said applicator section is substantially axially coincident with the stem.

6. The hand-held instrument of claim 1, wherein the lateral dimension of the adhesion surface of said applicator section is substantially axially coincident with the stem.

7. The hand-held instrument of claim 1, further comprising a removal section supported upon said second end of said wand-like stem, said removal section having a swab-like shape.

8. The hand-held instrument of claim 7, wherein said swab-like removal section is integrally formed with said wand-like stem, and is coated with a layer of adhesive-like material.

9. The hand-held instrument of claim 1, wherein said applicator section is wettable, and holds said medicinal insert by capillary action prior to placement in the eye.

10. A hand-held instrument for facilitating the application and/or removal of a medicinal substantially elliptically-shaped insert, to and from an eye, said instrument comprising:
    an elongated wand-like stem to be hand-held, said wand-like stem having an applicator end and a distal end opposite said applicator end;
    an applicator section supported upon said applicator end of said wand-like stem for receiving a medicinal substantially elliptically-shaped insert, and for placing said medicinal insert generally upon a sclerotic or eyelid portion of said eye, said applicator section having a capillary attraction type adhesion applicator surface area generally less than a surface area of said insert, and
    a removal section supported upon said distal end of the wand-like stem, said removal section having a swab-like shape, said removal section being coated with an adhesive for adhesively contacting and removing a medicinal substantially ellipitally-shaped insert which has been placed in the eye by said applicator section.

11. A hand-held instrument for facilitating the application and/or removal of a medicinal insert, to and from an eye, said instrument comprising:
    an elongated wand-like stem to be hand-held for applying said medicinal insert to said eye, said wand-like stem having an applicator end and a distal end opposite said applicator end;
    an applicator section supported upon said applicator end of said wand-like stem for receiving a medicinal insert, and for placing said medicinal insert generally upon a sclerotic or eyelid portion of said eye, said applicator section having a surface for adhering to said medicinal insert which exerts a force which is adhesively less than a force exerted by the sclerotic or eyelid portion of the eye upon said medicinal insert; and
    a removal section supported upon said distal end of the wand-like stem, said removal section having a surface for adhering to said medicinal insert which exerts a force which is adhesively greater than the force exerted by the sclerotic or eyelid portion of the eye upon said medicinal insert.

12. The hand-held instrument of claim 11, wherein said removal section has a swab-like shape.

13. The hand-held instrument of claim 11, wherein said removal section is coated with an adhesive material.

14. The hand-held instrument of claim 11, wherein said applicator section has a substantially elliptical shape.

15. The hand-held instrument of claim 11, wherein said applicator section has a surface area which is less than a surface area of said insert.

* * * * *